United States Patent [19]

Gorbunov et al.

[11] 4,017,518

[45] Apr. 12, 1977

[54] METHOD OF PREPARING 4,4-DIMETHYLDIOXANE-1,3

[76] Inventors: Boris Nikolaevich Gorbunov, prospekt Lenina 6, kv. 41; Galina Dmitrievna Efremova, ulitsa Sovetskaya 26, kv. 65, both of Volgograd; Evgeny Maximovich Kukartsev, ulitsa Kommunisticheskaya 38, kv. 18; Lidia Vladimirovna Erokhina, ulitsa Druzhby 12, kv. 49, both of Volzhsky Volgogradskoi; Anatoly Ivanovich Lukashov, ulitsa Palekhskaya 9, korpus 1, kv. 65, Moscow; Vitaly Vasilievich Orlyansky, ulitsa Sovetskaya 5, kv. 21, Volzhsky Volgogradskoi oblasti; Alexandr Pavlovich Khardin, ulitsa Krasnopiterskaya 2, kv. 32, Volgograd; Ideya Antonovna Churikova, prospekt Lenina 101, kv. 65; Daniil Iosifovich Valdman, ulitsa Sovetskaya 37, kv. 35, both of Volzhsky Volgogradskoi oblasti, all of U.S.S.R.

[22] Filed: Apr. 18, 1975

[21] Appl. No.: 569,388

Related U.S. Application Data

[63] Continuation of Ser. No. 484,788, July 1, 1974, abandoned.

[52] U.S. Cl. .................... 260/340.7; 260/635 R
[51] Int. Cl.² .................................. C07D 319/04
[58] Field of Search ........................ 260/340.7

[56] References Cited

UNITED STATES PATENTS

| 2,490,276 | 12/1949 | Munday et al. | 260/340.7 |
| 3,414,588 | 12/1968 | Jones | 260/340.7 |

FOREIGN PATENTS OR APPLICATIONS

| 475,546 | 7/1951 | Canada | 260/340.7 |

*Primary Examiner*—Ethel G. Love

[57] ABSTRACT

The method of preparing 4,4-dimethyldioxane-1,3 consists in the interaction of isobutylene and formaldehyde in an aqueous medium at from 90° to 115° C in the presence of a catalyst, the capacity of which such inorganic salts of mineral acids may be used with the pH value of the aqueous solutions whereof being within 2.2 to 4.5, resulting in the formation of an organic and an aqueous phase containing the end product, followed by the separation of said phases, washing the organic phase with water, and isolation of the end product.

When a catalyst of such salts is used, the acidity of the aqueous solutions of which is either invariable or decreases with an increase in the salt concentration, it is expedient that the aqueous phase and the wash water be evaporated to a level of from 85 to 90 percent to form a fraction containing the unreacted formaldehyde, and a distillation residue which is in fact an oil bed and a salt bed with the latter, after having been separated, being returned to the stage of interaction of the starting reagents.

3 Claims, No Drawings

METHOD OF PREPARING 4,4-DIMETHYLDIOXANE-1,3

This is a continuation of application Ser. No. 484,788 filed July 1, 1974, now abandoned.

The present invention relates to methods of preparing 4,4-dimethyldioxane-1,3.

Said 4,4-dimethyldioxane-1,3 finds extensive application in the chemical industry in, for instance, the synthesis of isoprene which is a starting monomer for sterospecific polyisoprene rubber.

An industrial method of preparing 4,4-dimethyldioxane-1,3 is known in the art (of. a monograph entitled "A new method of synthesis of divinyl-series dienes" by M.I. Farberov, Moscow, 1952 /in Russian/). The method consists in interaction of isobutylene and formaldehyde in an aqueous medium at a temperature of from 80° to 100° C and a pressure of from 16 to 20 atm. gauge in the presence of sulphuric acid as a catalyst. The method is carried out as follows; a reaction vessel composed of two series-connected tubular apparatus is inoculated, in countercurrents, with an isobutane fraction and a formaldehyde mix consisting at least 35 percent formaldehyde, and from 1.0 to 2.0 percent sulphuric acid. The resulting reaction products, viz., dimethyldioxane, diols, trimethyl-carbinol, methylal, unsaturated, and cyclic alcohols, and others, become distributed, depending upon their solubility, between the organic and aqueous phases, whereupon the phases are separated, with the organic phase being washed of the unreacted formaldehyde with a simultaneous neutralization of sulphuric, and formic acids with a weak alkaline solution, after which said phase is fed for rectification. During rectification, the following fractions are distilled off consecutively: hydrocarbons $C_4$, methylal-methanol, trimethyl-carbinol, and the end product. The aqueous phase is neutralized with an alkali, and subjected to rectification to isolate the high-volatile organic products, such as methylal, trimethylcarbinol, unreacted formaldehyde, dimethyldioxane, etc. The water containing the high-boiling organic compounds 3-methylbutanediol-1,3 inclusive, and the sulphates, is discarded into sewerage. The isobutylene conversion level is, on an average, from 80 to 82 percent, that of formaldehyde, from 84 to 86 percent. The yield of the end product in terms of the converted formaldehyde is from 80 to 82 percent, and that in terms of isobutylene, from 68 to 70 percent.

The disadvantages inherent in said known method reside in the presence of large amounts of by-products that are liable to form during the reaction, thus necessitating the neutralization of the organic and aqueous phases, disposal of large quantities of sewage water containing a great proportion of high-boiling organic products, and sodium sulphate; a problem also arises concerned with ridding the water phase of organic compounds.

It is an essential object of the present invention to develop a method of preparing 4,4-dimethyldioxane-1,3 such that would make it possible to render the process more selective.

It is another object of the present invention to increase the yield of the end product due to the extraction of 3-methylbutanediol-1,3, as well as to completely eliminate process waste water.

According to said and other objects, the invention consists in that isobutylene is reacted with formaldehyde in an aqueous medium in the presence of a catalyst at a temperature of from 90° to 115° C to form organic and aqueous phases whereupon the organic phase is washed with water and the end product isolated. According to the invention, the catalyst used are inorganic salts of mineral acids featuring a pH value of from 2.2 to 4.5 within this aqueous solution.

The process carried out in the presence of said salts under the above-specified conditions results in a reduced total amount of high-boiling products, i.e., in a higher selectivity for the process.

The proposed method enables the process to be run with catalyst recycling.

In order to effect catalyst recycling, it is expedient to use, as the latter said salts, the acidity of the aqueous solutions which is either invariable or reduced with an increase in the salt concentration.

The recycling of a salt catalyst is accounted for by the fact that the acidity of the aqueous phase and wash water remains invariable, or decreases despite an increase in the salt concentration due to heating. This is not accompanied by resinification of organic products, so that 4,4-dimethyldioxane-1,3 possessing the least hydrolytic stability in acidic media, as well as other products contained in the aqueous phase, exhibit chemical stability when heated.

It is expedient, for the purpose of returning the salt catalyst into the reaction and ruling out the waste water from the process, that the aqueous phase and wash water be evaporated to a level of from 85 to 90 percent so to form a fraction containing the unreacted formaldehyde, and a distillation residue which is essentially an oil bed containing high-boiling organic products, and a salt bed which, after having been separated, is returned, together with the unreacted formaldehyde after having been recovered, to the stage of the reaction of the starting reagents. Thus, the evaporation process enables the waste water of the process to be completely eliminated.

A further amount of 4,4-dimethyldioxane-1,3 is also formed during the evaporation process, this being due to the fact that no resinification of the organic products occurs in the presence of the abovesaid salts, which also makes it possible to use 3-methylbutanediol-1,3 for preparing the end product which is formed as reaction by-product with a yield of from 30 to 35 percent with respect to the reacted formaldehyde. When evaporating the synthesis aqueous reaction phase, and the wash water after washing the organic phase in the presence of said salts, 3-methylbutanediol-1,3 is completely converted into the end product due to its being reacted with the unreacted formaldehyde contained in the aqueous phase, according to the following reaction diagram:

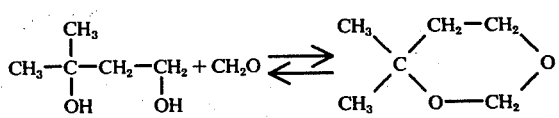

The procedure ensures from all discussed above that 4,4-dimethyldioxane-1,3 can be prepared from 3-methylbutanediol-1,3 in the presence of said salt catalysts.

Thus, as compared to the known method, the herein proposed method enables high-level (up to 85–90 percent) evaporation of the aqueous reaction phase with subsequent separation of the oil bed from the salt solution, with feeding the latter to the stage of interaction of the starting reagents (catalyst recycling). Carrying out the process utilizing catalyst recycling enables practically a complete elimination of the organic waste products together with sewage water, and thus attaining a higher selectivity of the process due to the use of 3-methylbutanediol-1,3 which has previously been wasted with sewage water. The yield of the end product is increased, as contrasted to the known method, which amounting to from 88 to 90 percent with respect to the reacted formaldehyde. The data illustrating the process with recycling the salt catalyst are given in Tables 1 and 2 hereinbelow.

The proposed method is carried into effect preferably as follows:

A starting catalyst is used in the form of an aqueous solution of an inorganic salt whole amount, due to the catalyst recycling according to a closed-circulation circuit, is proportioned by proceeding from an initial filling of the recycle circuit and subsequent slight replenishing there of so to compensate for the catalyst mechanical losses.

The starting formaldehyde mixture, which is an aqueous formaldehyde and salt solution, containing from 35 to 45 percent formaldehyde, and from 2.0 to 2.5 percent anhydrous salt, is prepared by mixing the solutions of both. In catalyst recycling, for the preparation of the formaldehyde mixture, a salt solution resulting from the evaporation of the synthesis aqueous phase is used.

ratus of the column type, with settling zones provided in the top and bottom portions thereof. The formaldehyde mixture and isobutylene or an isobutane-isobutylene fraction, containing from 45 to 50 percent by weight isobutylene, are introduced into the reaction vessel countercurrently. The reaction occurs in the tubular portion of the reaction vessel at from 90° to 115° C.

The reaction provides an organic and an aqueous phase. The organic phase, containing organic products and C4 hydrocarbons is discharged from the top settling portion of the reaction vessel, washed with water fed in countercurrent, and is then fed for a multistage rectification to isolate the end product, while the wash water, the aqueous phase of the synthesis, and the discharged from the bottom settling zone of the reaction vessel, is fed for processing which consists in isolating the light organic fractions with subsequent high-level evaporation (to 85–90 percent) in order to yield a further amount of the end product due to the conversion of 3-methylbutanediol-1,3, and stratification of the reaction mass into an oil bed, and a salt bed (a saturated salt solution) which is returned, after being separated from the oil bed, to the stage of interaction of the starting reagents (catalyst recycling). The evaporation fraction is fed for formaldehyde recovery, whereupon the recycle formaldehyde is fed to the stage of preparing the formaldehyde mix.

The salts proposed as catalysts can be useful in inter-reactions of an aqueous formaldehyde with a concentrated isobutylene and an isobutane-isobutylene frac- Table 1

Data on salt catalyst recycling, involving high-level evaporation of the aqueous reaction phase /catalyst-$Cr_2(SO_4)_3$/. Reaction temperature - 95°, reaction time 80 min., molar ratio of $iC_4H_8$ to $CH_2O$ - 1.15, starting amount of catalyst is 2.5%

| Recycle No. | $CH_2O$ conversion percentage | $CH_2O$ concentration in starting mixture,% | Yield of 4,4-dimethyl-dioxane-1,3,% | Percentage of high-boiling products in organic phase | Amount of recycled salt solution, % of aqueous phase and wash water |
|---|---|---|---|---|---|
| 1 | 90.1 | 42.0 | 87.8 | 5.82 | 5.86 |
| 2 | 88.7 | 41.9 | 88.3 | 5.29 | 5.45 |
| 3 | 88.1 | 40.7 | 88.2 | 5.23 | 5.26 |
| 4 | 87.3 | 41.2 | 87.9 | 4.86 | 5.85 |
| 5 | 87.8 | 41.7 | 89.6 | 4.36 | 4.94 |
| 6 | 86.3 | 40.9 | 88.6 | 4.25 | 4.67 |
| 7 | 87.3 | 41.2 | 88.9 | 4.10 | 4.83 |
| 8 | 86.4 | 39.4 | 88.2 | 4.02 | 4.75 |
| 9 | 86.2 | 40.2 | 88.1 | 4.11 | 5.85 |
| 10 | 86.9 | 40.8 | 88.9 | 4.10 | 5.71 |

Table 2

Data on variation of 3-methylbutanediol-1,3 content as a result of heating the aqueous phase of 4,4-dimethyl-dioxane-1,3 synthesis in the presence of chromium sulphate (reaction time - 2 hours, temperature 100° C)

| Description | 3-methyl-butanediol-1,3 | | 4,4-dimethyl-dioxane-1,3 | | $CH_2O$ | | Dioxane alcohols | | $H_2O$ | |
|---|---|---|---|---|---|---|---|---|---|---|
| | % | g | % | g | % | g | % | g | % | g |
| Starting test | 7.5 | 10.6 | none | none | 23.7 | 33.4 | 29.5 | 41.6 | 39.3 | 55.4 |
| Postreaction analysis | none | none | 7.8 | 11.0 | 19.6 | 27.7 | 29.5 | 41.6 | 43.1 | 60.7 |

The reaction is run in the liquid phase in a reaction vessel composed of two series-connected tubular appation, containing from 45 to 50 weight percent isobutylene. The formaldehyde conversion level attained is quite suitable for industrial conditions (refer to Table 3 below).

Table 3

Formaldehyde conversion percentage and selectivity of 4,4-dimethyldioxane-1,3 synthesis in the presence of aluminium sulphate versus reaction temperature

| Nos | Conditions of synthesis | | | Conversion percentage of $CH_2O$ | Yield percentage of 4,4-dimethyl-dioxane-1,3 |
|---|---|---|---|---|---|
| | temperature, °C | reaction time, hours | isobutyelene concentration,% | | |
| 1 | 80 | 2 | 99.2 | 37.3 | 87.2 |
| 2 | 100 | 2 | 99.2 | 79.7 | 85.7 |
| 3 | 110 | 2 | 99.2 | 85.3 | 85.4 |
| 4 | 120 | 2 | 99.2 | 91.0 | 83.8 |
| 5 | 110 | 1 | 46.0 | 60.0 | 81.6 |
| 6 | 120 | 1 | 47.0 | 93.0 | 83.8 |
| 7 | 130 | 0.5 | 47.0 | 88.0 | 85.4 |

In order to promote better understanding of the present invention, given below are the following examples of practical embodiment thereof.

EXAMPLE 1

The preparation of 4,4-dimethyldioxane-1,3 in the presence of trivalent-chrominum sulphate with the use of a concentrated isobutylene A stainless-steel reaction vessel equipped with a stirrer, a thermocouple, and heating-and-cooling jacket is inoculated with 776.5 g of a formaldehyde mix in the form of a 38.2 percent aqueous formaldehyde solution, containing 3 weight percent $Cr_2(SO_4)_3 \cdot 6H_2O$, and 930 g of preliminarily condensed isobutylene with a 99.8-percent concentration. The reaction mixture is heated to 90° C and stirred at that temperature for 60 minutes. After having been cooled the reaction mass is separated into organic and aqueous phases. From the organic phase, after its having been washed with water, the end product is rectification-isolated, whereas the wash water is mixed with the aqueous phase, and vacuum-evaporated to a 85-percent level. The resultant distillation residue is stratified, whereupon the salt bed is separated from the oil bed and fed as a catalyst to the stage of interaction of the starting reagents. The evaporation fraction is fed to formaldehyde recovery which is then also returned for the stage of interaction of the starting reagents.

The yield of end product equals 89.1 percent with respect to the reacted formaldehyde, with the formaldehyde conversion percentage being 96.3.

EXAMPLE 2

The preparation of 4,4-dimethyldioxane-1,3 in the presence of trivalent-chromium sulphate with the use of an isobutane-isobutylene fraction 770 g of formaldehyde mix are introduced into a stainless-steel reaction vessel provided with a stirrer, a thermocouple and a heating-and-cooling jacket mix being in the form of an aqueous formaldehyde, and chromium sulphate solution, containing 40 percent formaldehyde and 3 percent $Cr_2(SO_4)_3 \cdot 6H_2O$, and 1300 g of a preliminarily condensed isobutane-isobutylene fraction containing 47.4 weight percent isobutylene. The experiment is run at 95° C for 80 minutes similarly to that as described in Example 1.

The yield of with the end product is 88.25 percent, the formaldehyde conversion level being 90.55 percent.

EXAMPLE 3

The preparation of 4,4-dimethyldioxane-1,3 in the presence of chromic potassium sulphate A preliminarily cooled stainless-steel flask is inoculated with 37 g formalin having a 36.5-percent concentration, 0.708 g $K_2Cr_2/SO_4/_4 \cdot 24H_2O$, and 17.5 g of a condensed liquid isobutylene having a 99.8-percent concentration. Then the hermetically sealed flask is placed, for the reaction time, into a temperature-controlled cabinet provided with a shaker heated to 105° C, whereupon the shaker is put into operation. The reaction time is 2 hours from the starting of the shaker. Upon termination of the reaction the flask is quickly cooled and the resultant organic phase, after stratification, is separated from the aqueous phase, whereupon the end product is isolated from the reaction phases.

The yield of the end product is 83.9 percent, with the formaldehyde conversion level being 88.65 percent.

EXAMPLE 4

The preparation of 4,4-dimethyldioxane-1,3 in the presence of ferriammonium sulphate A preliminarily cooled stainless-steel flask is inoculated 37 g formalin having a 36.25-percent concentration, 0.602 g $FeSO_4/NH_4/_2SO_4 \cdot 6H_2O$, and 17.5 g of a condensed liquid isobutylene having a 99.8-percent concentration. The experiment is run similarly to that as described in Example 1.

The yield of the end product is 85.7 percent, with the formaldehyde conversion level being 81.05 percent.

EXAMPLE 5

The preparation of 4,4-dimethyldioxane-1,3 in the presence of potassium bifluoride A stainless-steel reaction vessel provided with a stirrer, a thermocouple and a heating-and-cooling jacket is inoculated with 258.8 g of a formaldehyde mix which mix is essentially an aqueous formaldehyde and potassium bifluoride solution containing 40 percent formaldehyde, and 3 percent $KHF_2$, and 310 g of a preliminarily condensed isobutylene having a 99.8-percent concentration. The experiment proceeds at 95° C for 2 hours as described in Example 1.

The yield of the end product is 80 percent, with the formaldehyde conversion level being 91.2 percent.

EXAMPLE 6

The preparation of 4,4-dimethyldioxane-1,3 in the presence of aluminium nitrate

A stainless-steel reaction vessel provided with a stirrer, a thermocouple and a heating-and-cooling jacket is inoculated with 517 g of a formaldehyde mix, viz., a 39-percent aqueous formalin solution, containing 3 weight percent $Al_3(NO_3)_3 \cdot 9H_2O$, and 620 g of a preliminarily condensed isobutylene having 99.8-percent concentration. The experiment is run at 95° C for two hours as described in Example 1.

The yield of 4,4-dimethyldioxane-1,3 is 65 percent, that of unsaturated alcohols, 15 percent, isoprene, 10 percent. The formaldehyde conversion level is 95 percent.

EXAMPLE 7

The preparation of 4,4-dimethyldioxane-1,3 in the presence of chromium trichloride A stainless-steel reaction vessel provided with a stirrer, a thermocouple, and a heating-and-cooling jacket is inoculated with 776.5 g of a formaldehyde mix, viz., a 40-percent aqueous formalin solution, containing 3 weight percent $CrCl_3 \cdot 10H_2O$, and 930 g of a preliminarily condensed isobutylene having a 99.8-percent concentration. The experiment occurs at 95° C for 2 hours as described in Example 1.

The 4,4-dimethyldioxane-1,3 yield is 78 percent, with the formaldehyde conversion percentage being 87.3.

What is claimed is:

1. A method of preparing 4,4-dimethyldioxane-1,3 comprising reacting isobutylene with formaldehyde in an aqueous medium at 90°–115° C in the presence of a catalyst comprising inorganic salts of mineral acids, whose aqueous solutions have a pH value of from 2.2 to 4.5 and whose acidity of said aqueous solutions does not increase with an increase in the salt concentration said inorganic salts being selected from the group consisting of chromium sulfate, chromic potassium sulfate, ferriamonium sulfate, potassium bifluoride, aluminum nitrate, and chromium trichloride, to form organic and aqueous phases containing the end product; separating said phases; washing the organic phase with water; and isolating the end product.

2. The method as claimed in claim 1, wherein the aqueous phase and wash water are evaporated to a level of from 85 to 90 percent to form a fraction containing the unreacted formaldehyde, and a distillation residue, which is an oil bed, and a salt bed, with the latter, after having been separated, being returned to the stage of reaction of the starting reagents.

3. A method as claimed in claim 2, wherein the unreacted formaldehyde is recovered from the fraction and returned to the stage of reacting of the starting reagents.

* * * * *